United States Patent [19]

Beller et al.

[11] Patent Number: 5,756,727

[45] Date of Patent: May 26, 1998

[54] CHIRAL MANGANESE TRIAZONONANE COMPLEXES

[75] Inventors: Matthias Beller, Idstein; Ahmed Tafesh, Kelkheim; Richard Walter Fischer, Bad Soden; Bernd Scharbert, Frankfurt, all of Germany

[73] Assignee: Hoechst AG, Germany

[21] Appl. No.: 671,957

[22] Filed: Jun. 28, 1996

[30] Foreign Application Priority Data

Jun. 30, 1995 [DE] Germany ............... 195 23 891.5

[51] Int. Cl.$^6$ .................................................. C07D 403/02
[52] U.S. Cl. ...................................... 540/474; 540/465
[58] Field of Search ............................ 540/474, 465, 540/470

[56] References Cited

U.S. PATENT DOCUMENTS

| | | |
|---|---|---|
| 5,247,075 | 9/1993 | Parker et al. ............... 540/465 |
| 5,256,779 | 10/1993 | Kershner et al. ............ 540/465 |
| 5,280,117 | 1/1994 | Kershner et al. ............ 540/465 |
| 5,462,725 | 10/1995 | Kiefer et al. ............... 424/9.363 |
| 5,484,893 | 1/1996 | Parker et al. ............... 530/391.5 |

OTHER PUBLICATIONS

Wieghardt et al., J. Amer. Chem. Soc; 1988, 110, pp. 7398–7411.

*Primary Examiner*—Mukund J. Shah
*Assistant Examiner*—Pavanaram K. Sripada
*Attorney, Agent, or Firm*—Connolly & Hutz

[57] ABSTRACT

The chiral manganese-triazonone complex of the general formula (I) is disclosed:

$$[Mn_u(L)_v(OR)_w(\mu\text{-}O)_x(\mu OAc)_y]X_z \qquad (I)$$

The complex is useful industrially to prepare chiral compounds.

10 Claims, No Drawings

CHIRAL MANGANESE TRIAZONONANE COMPLEXES

Stereoselective oxidation reactions are of central importance for the synthesis of a large number of active substances and active substance intermediates for drugs and agrochemicals. Epoxidation reactions in particular are an important method for preparing chiral compounds because the products can be functionalized in a variety of ways.

There is at present no general process which makes chiral compounds available both in high yields and in high enantioselectivities.

It is furthermore unsatisfactory, especially from the industrial viewpoint, that all catalyst systems disclosed to date have only extremely poor catalyst turnover numbers, so that large amounts of catalyst—as a rule between 5 and 10 mol %—must be used.

For the stated reasons there was great industrial interest in developing better catalyst systems which can be used industrially to prepare chiral compounds.

The object is achieved by chiral manganese-triazanonane complexes of the formula (I)

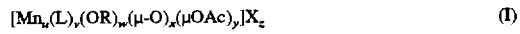

in which:

u and v are 1 or 2;

w, x and y are 0, 1, 2 or 3;

z is 1, 2 or 3 with the proviso that v is 1, w is 1, 2 or 3, z is 1, 2 or 3 when u is 1, or v is 2, w is 0 or 1, x is 1, y is 2, z is 1 or 2, or v is 2, w is 0 or 1, x is 1, y is 2, z is 2 or 3, or v is 2, w is 0 or 1, x is 3, y is 0, z is 1 or 2, when u is 2;

R is $(C_1-C_2)$alkyl,

X is $PF_6^\ominus$, $F^\ominus$, $Cl^\ominus$, $Br^\ominus$, $I^\ominus$, $(C_6H_5)B^\ominus$, $ClO_4^\ominus$, L is a chiral organic triazanonane ligand of the formula (II),

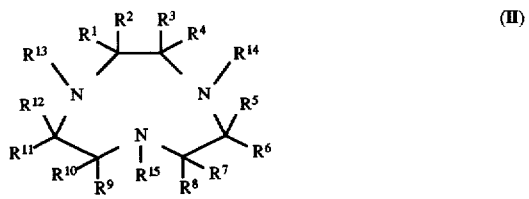

in which $R^1$ to $R^{12}$ are, independently of one another, hydrogen, $(C_1-C_{12})$alkyl, $(C_3-C_{12})$cycloalkyl, $(C_1-C_{12})$alkenyl, $(C_1-C_{12})$alkoxy, $(C_1-C_{12})$acyloxy, aryl, heteroaryl, $CH_2$-aryl, COOH, COO$(C_1-C_{12})$alkyl, COO-aryl, CN, halogen, C-(halogen)$_3$, $NH_2$, NH-$(C_1-C_{12})$-alkyl, $N(C_1-C_{12}$-alkyl$)_2$, NH-aryl, N(aryl)$_2$, N-alkylaryl, $S(C_1-C_{12})$alkyl, $SO(C_1-C_{12})$alkyl, $SO_2(C_1-C_{12})$alkyl, $P(C_1-C_{12}$alkyl$)_2$ and $R^{13}$ to $R^{15}$ are hydrogen, $(C_1-C_{12})$alkyl, $CH_2$-aryl, aryl and heteroaryl.

Compounds of interest are those in which formula (I) is

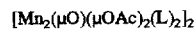

where for ligand L in formula (II) $R^1$ to $R^{12}$ are, independently of one another, hydrogen, $(C_1-C_6)$alkyl, $(C_3-C_6)$cycloalkyl, $(C_1-C_6)$alkoxy, phenyl, naphthyl, tolyl, pyridyl, bipyridyl, benzyl, COO$(C_1-C_6)$alkyl, N$(C_1-C_6$-alkyl$)_2$ or NH-phenyl and $R^{13}$ to $R^{15}$ are hydrogen, $(C_1-C_{12})$alkyl, phenyl, tolyl, benzyl, pyridyl or bipyridyl.

Particularly important compounds in this connection are those in which, for the ligand L, $R^1$ to $R^{12}$ are hydrogen, $(C_1-C_6)$alkyl, $(C_3-C_6)$cycloalkyl, phenyl, benzyl, pyridyl, bipyridyl or N$(C_1-C_6$-alkyl$)_2$ and $R^{13}$ to $R^{15}$ are hydrogen, $(C_1-C_6)$alkyl, phenyl, benzyl or pyridyl.

The compounds according to the invention can be prepared by several processes. One method comprises adding a 1.1 to 1.5-fold excess of a manganese (III) salt at a pH of 7 to 9 to the ligand L, dissolved in a polar solvent, adjusting the resulting solution to pH 4 to 6 with an acid HX, and precipitating the target compound by adding a nonpolar solvent.

It has proven suitable in this case to use manganese(III) acetate as manganese(III) salt, a mixture of $(C_1-C_3)$ alcohols and water as polar solvent, $HPF_6$ as acid HX, and a hydrocarbon as nonpolar solvent.

Another method comprises adding ligand L with cooling to an alcoholic solution of a manganese (II) salt, adding an excess of alkali metal alcoholate, and oxidizing the complex which is formed, with addition of NaX, using air, and isolating it by extraction.

It has proven suitable in this case to use sodium methoxide as alkali metal alcoholate, $NaPF_6$ as salt NaX, and an acetonitrile/heptane mixture as extractant.

Synthesis of the ligands:

EXAMPLE 1

Synthesis of bis-N,N-(2-tosyloxyethyl)-p-toluenesulfonamide

A 1 l three-necked flask with mechanical stirrer, reflux condenser, internal thermometer and 1 l dropping funnel is charged with 115.0 g (0.603 mol) of p-toluenesulfonyl chloride and 300 ml of pyridine. The mixture is stirred and heated to 50° C. in order to dissolve the solid. The reaction vessel is subsequently immersed in a water bath at 30° C. Then a solution of 21.0 g (0.20 mol) bis-N,N-(2-hydroxyethyl)amine in 30 ml of pyridine is added in such a way that the reaction temperature is between 50° and 60° C. The mixture is stirred at this temperature for a further 90 minutes and subsequently poured into ice-water. Bis-N,N-(2-tosyloxyethyl)-p-toluenesulfonamide is filtered off in a yield of 90%.

EXAMPLE 2

Synthesis of bis-N,N'-tosyl-1,2-diaminocyclohexane

A 1 l three-necked flask with mechanical stirrer, reflux condenser, internal thermometer and 1 l dropping funnel is charged with 171.9 g (0.90 mol) of p-toluenesulfonyl chloride and 300 ml of pyridine. The mixture is heated to 50° C. to dissolve the solid. The reaction vessel is subsequently immersed in a water bath at 30° C. Then a solution of 50.0 g (0.438 mol) of trans-1,2-di-aminocyclohexane in 50 ml pyridine is added in such a way that the reaction temperature is between 50° and 60° C. The mixture is stirred at this temperature for a further 90 minutes and subsequently poured into ice-water. Bis-N,N'-tosyl-1,2-diaminocyclohexane is filtered off in a yield of 90%.

EXAMPLE 3

Synthesis of 1,4,7-tris-tosyl-2,3-cyclohexano-1,4,7-triazacyclononane 100 g (0.236 mol) of bis-N,N'-tosyl-1,2-diaminocyclohexane are suspended in 300 ml of ethanol in a 1 l 3-necked flask. After heating to reflux, 330 ml of a 1.5 N sodium methanolate solution are rapidly added dropwise. This solution is then decanted into an Erlenmeyer flask. After cautious evaporation in vacuo, the disodium salt of bis-N,N'-tosyl-1,2-diaminocyclohexane crystallizes out in a yield of 90%. 80 g (0.17 mol) of the disodium salt are then transferred into a 1 l 3-necked flask and dissolved in 500 ml of dimethylformamide. The reaction mixture is heated to 100° C., and 97 g (0.17 mol) of bis-N,N-(2-tosyloxyethyl)-p-toluenesulfonamide in 300 ml of dimethylformamide are added dropwise. After the addition is complete, the mixture is stirred at 100° C. for a further hour and then cooled to room temperature. Aqueous work-up and crystallization result in the desired product in a yield of 68%

EXAMPLE 4

Synthesis of 2,3-cyclohexano-1,4,7-triazacyclononane 50 g of the chiral cyclic triazanonane derivative is mixed with 200 ml of concentrated sulfuric acid. The reaction mixture is heated to 100° C. and stirred at this temperature for 70 hours. After cooling to 0° C., 500 ml of diethyl ether are cautiously added. The precipitated salt is filtered off under nitrogen and washed with anhydrous diethyl ether. The salt is then added to 200 ml of water and neutralized with 30 ml of a 50% strength sodium hydroxide solution. The solution is heated with 3 g of active carbon to 80° C. and filtered through Celite. The filtrate is cooled in ice and adjusted to pH1 by adding sulfuric acid. The product which precipitates thereby is filtered off and recrystallized from acetonitrile for further purification. The required product is obtained in a yield of 71%.

MS (EI, 70 eV): M+H$^+$ 184 (100%)

Elemental analysis: calculated C 65.53 H 11.55 N 22.93 found C 65.41 H 11.32 N 22.58

EXAMPLE 5

Synthesis of 1,4,7-trimethyl-2,3-cyclohexano-1,4,7-triazacyclononane (=ligand L)

20.0 g (88.4 mmol) of 2,3-cyclohexano-1,4,7-triazacyclononane are dissolved in 50 ml of dichloromethane in a 100 ml three-necked flask. 25.5 g of methyl iodide (266 mmol) are added dropwise to the reaction mixture over the course of 30 minutes. The mixture is subsequently refluxed for 12 hours, cooled and filtered. After extraction with 100 ml of water three times, the organic base is dried with magnesium sulfate. Removal of this solvent by distillation in vacuo results in the required product, which can be further purified by chromatography on silica gel with ethyl acetatel/hexane (1:1) as eluent. Yield: 80%

MS (EI, 70 eV): M+H$^+$ 226 (100%)

Elemental analysis: calculated C 69.28 H 12.08 N 18.64 found C 68.98 H 11.95 N 18.43

Synthesis of the complexes

EXAMPLE 6

Synthesis of [Mn(L)(OMe)$_3$]PF$_6$
(Catalyst A)
(L=1,4,7-Trimethyl-2,3-cyclohexano-1,4,7-triazacyclononane, Example 5)

A solution, cooled to 0° C., of 2.25 g (10 mmol) of ligand L in 50 ml of anhydrous methanol is transferred under an inert gas into a suspension of 1.26 g (10 mmol) of anhydrous MnCl$_2$ in 10 ml of anhydrous methanol and stirred for about 30 minutes. At the same time, 1.53 g (15 mmol) of sodium are dissolved in methanol, the methanol is evaporated, and the above reaction solution is transferred under an inert gas at 0° C. through a frit onto the remaining white residue. The mixture is left to stir for about a further 20 minutes and then 3.36 g (20 mmol) of sodium hexafluorophosphate dissolved in 20 ml of methanol are added to the reaction mixture, which is then brought into the air, warmed to room temperature and evaporated to about one half, and a little n-heptane is added. The precipitated residue is suspended in acetonitrile and filtered, the filtrate is concentrated and then a little n-heptane is added. A brown powder precipitates and is filtered off and dried to afford 1.34 g (26%).

Elemental analysis: calculated C 37.0 H 7.0 N 8.1 Mn 10.6 found C 38.1 H 7.3 N 8.0 Mn 9.9

Melting point: >300° C. (decomposition)

EXAMPLE 7

Synthesis of [Mn$_2$(μ-O)(μ-OAc)$_2$(L)$_2$][PF$_6$]$_2$
(Catalyst B)

2.25 g (10 mmol) of ligand L are dissolved under an inert gas at room temperature in 60 ml of an ethanol/water (90/10 v/v) mixture, 3.22 g (12 mmol) of manganese(III) acetate dihydrate are added and firstly the pH is adjusted to 8 by adding sodium acetate and then adjusted to pH 5 by cautious dropwise addition of concentrated HPF$_6$ solution. The mixture is left to stir for about 10 minutes and then 3.36 g (20 mmol) of sodium hexafluorophosphate is added in solid form to the reaction mixture, which is stirred for about a further 10 minutes, and a little n-heptane is added. The precipitated residue is suspended in acetonitrile and filtered, and the filtrate is concentrated and then a little n-heptane is added. This procedure is repeated twice. A red powder precipitates and is filtered off and dried to afford 0.81 g (16%).

Elemental analysis: calculated C 36.7 H 6.2 N 8.6 0 8.2 Mn 10.4 found C 36.1 H 6.3 N 8.3 0 8.5 Mn 10.0

Melting point: >300° C. (decomposition)

EXAMPLE 8

Synthesis of [Mn$_2$(μ-O)(μ-OAc)$_2$(L)$_2$][PF$_6$]$_3$
(Catalyst C)

200 mg (0.2 mmol) of the manganese complex from Example 7 are dissolved in 30 ml of a 0.1 M solution of tetrabutylammonium hexafluorophosphate (conducting salt) in acetonitrile, introduced into the anode chamber of a two-electrode cell which is divided by a ®Nafion membrane and has a Pt anode, and electrolyzed at a constant current density of 5 mA/cm$^2$. After 0.96 Faraday/mol has passed through, the cell voltage increases very greatly. The electrolysis is stopped at this time, the color of the anolyte having changed from the initial dark red to greenish brown. The electrolysis solution is concentrated, and the residue is washed with ethanol/water and recrystallized from acetonitrile/n-heptane. The product is contaminated with a little conducting salt.

Yield: 280 mg.

EXAMPLE 9

Synthesis of [Mn$_2$(μ-O)$_3$(L)$_2$][PF$_6$]$_2$ (Catalyst D) 200 mg (0.2 mmol) of the manganese complex from Example 2 are dissolved in 30 ml of ethanol/water (1/1, v/v) as mixture with sonication and, after addition of 2 ml of triethylamine and 2 g of solid sodium hexafluorophosphate, are stirred in air for a few minutes. The reaction mixture is filtered and the filtrate is evaporated. The remaining residue is dissolved in a little acetonitrile and filtered, and the evaporated filtrate is recrystallized again from acetonitrile/ n-heptane. 80 mg of red needles remain.

Elemental analysis: calculated: C 33.8 H 5.9 N 9.1 O 8.7 Mn 11.1 experimental: C 34.5 H 6.0 N 8.9 O 8.8 Mn 10.7

We claim:

1. A chiral manganese-triazanonane complex of the formula (I)

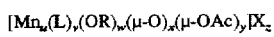

in which:

u and v are 1 or 2;

w, x and y are 0, 1, 2 or 3;

z is 1, 2 or 3 with the proviso that v is 1, w is 1, 2 or 3, z is 1, 2 or 3 when u is 1, or v is 2, w is 0 or 1, x is 1, y is 2, z is 1 or 2, or v is 2, w is 0 or 1, x is 1, y is 2, z is 2 or 3, or v is 2, w is 0 or 1, x is 3, y is 0, z is 1 or 2, when u is 2;

R is $(C_1-C_{12})$alkyl,

X is $PF_6^{\ominus}$, $F^{\ominus}$, $Cl^{\ominus}$, $Br^{\ominus}$, $I^{\ominus}$, $(C_6H_5)B^{\ominus}$, $ClO_4^{\ominus}$, L is a chiral organic triazanonane ligand of the formula (II),

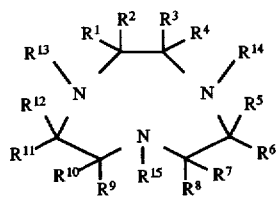

in which $R^1$ to $R^{12}$ are, independently of one another, hydrogen, $(C_1-C_{12})$alkyl, $(C_3-C_{12})$cycloalkyl, $(C_1-C_{12})$alkenyl, $(C_1-C_{12})$alkoxy, $(C_1-C_{12})$acyloxy, aryl, heteroaryl, $CH_2$-aryl, COOH, $COO(C_1-C_{12})$alkyl, COO-aryl, CN, halogen, C-(halogen)$_3$, $NH_2$, $NH-(C_1-C_{12})$-alkyl, $N(C_1-C_{12}$-alkyl$)_2$, NH-aryl, N(aryl)$_2$, N-alkylaryl, $S(C_1-C_{12})$alkyl, $SO(C_1-C_{12})$alkyl, $SO_2(C_1-C_{12})$alkyl, $P(C_1-C_{12}$alkyl$)_2$ and $R^{13}$ to $R^{15}$ are hydrogen, $(C_1-C_{12})$alkyl, $CH_2$-aryl, aryl and heteroaryl.

2. A compound as claimed in claim 1 of the formula

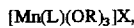

where for ligand L in formula (II) $R^1$ to $R^{12}$ are, independently of one another, hydrogen, $(C_1-C_6)$alkyl, $(C_3-C_6)$ cycloalkyl, $(C_1-C_6)$alkoxy, phenyl, naphthyl, tolyl, pyridyl, bipyridyl, benzyl, $COO(C_1-C_6)$alkyl, $N(C_1-C_6$-alkyl$)_2$ or NH-phenyl and $R^{13}$ to $R^{15}$ are hydrogen, $(C_1-C_{12})$alkyl, phenyl, tolyl, benzyl, pyridyl or bipyridyl.

3. A compound as claimed in claim 1 of the formula

where for ligand L in formula (II) $R^1$ to $R^{12}$ are, independently of one another, hydrogen, $(C_1-C_6)$alkyl, $(C_3-C_6)$ cycloalkyl, $(C_1-C_6)$alkoxy, phenyl, naphthyl, tolyl, pyridyl, bipyridyl, benzyl, $COO(C_1-C_6)$alkyl, $N(C_1-C_6$-alkyl$)_2$ or NH-phenyl and $R^{13}$ to $R^{15}$ are hydrogen, $(C_1-C_{12})$alkyl, phenyl, tolyl, benzyl, pyridyl or bipyridyl.

4. A compound as claimed in claim 1 of the formula

where for ligand L in formula (II) $R^1$ to $R^{12}$ are, independently of one another, hydrogen, $(C_1-C_6)$alkyl, $(C_3-C_6)$ cycloalkyl, $(C_1-C_6)$alkoxy, phenyl, naphthyl, tolyl, pyridyl, bipyridyl, benzyl, $COO(C_1-C_6)$alkyl, $N(C_1-C_6$-alkyl$)_2$ or NH-phenyl and $R^{13}$ to $R^{15}$ are hydrogen, $(C_1-C_{12})$alkyl, phenyl, tolyl, benzyl, pyridyl or bipyridyl.

5. A compound as claimed in claim 1 of the formula

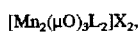

where for ligand L in formula (II) $R^1$ to $R^{12}$ are, independently of one another, hydrogen, $(C_1-C_6)$alkyl, $(C_3-C_6)$ cycloalkyl, $(C_1-C_6)$alkoxy, phenyl, naphthyl, tolyl, pyridyl, bipyridyl, benzyl, $COO(C_1-C_6)$alkyl, $N(C_1C_6$-alkyl$)_2$ or NH-phenyl and $R^{13}$ to $R^{15}$ are hydrogen, $(C_1-C_{12})$alkyl, phenyl, tolyl, benzyl, pyridyl or bipyridyl.

6. A compound as claimed in claim 1, wherein for the ligand L, $R^1$ to $R^{12}$ is hydrogen, $(C_1-C_6)$ alkyl, $(C_3-C_6)$cycloalkyl, phenyl, benzyl, pyridyl, bipyridyl or $N(C_1-C_6)$alkyl$_2$ and $R^{13}$ to $R^{15}$ are hydrogen, $(C_1-C_6)$alkyl, phenyl, benzyl or pyridyl.

7. A process for the preparation of a compound as claimed in claim 1, which comprises adding a 1.1 to 1.5-fold excess of a manganese (III) salt at a pH of 7–9 to the ligand L, dissolved in a polar solvent, adjusting the resulting solution to pH 4 to 6 with an acid HX, and precipitating the target compound by adding a nonpolar solvent.

8. A process as claimed in claim 7, wherein manganese (III) acetate is used as manganese(III) salt, and a mixture of $(C_1-C_3)$ alcohols and water is used as polar solvent, $HPF_6$ is used as acid HX and a hydrocarbon is used as nonpolar solvent.

9. A process for the preparation of a compound as claimed in claim 1, which comprises adding ligand L with cooling to an alcoholic solution of a manganese(II) salt, adding an excess of alkali metal alcoholate, and oxidizing the complex which is formed, with addition of NaX, using air, and isolating it by extraction.

10. The process as claimed in claim 9, wherein sodium methoxide is used as alkali metal alcoholate, $NaPF_6$ is used as salt NaX and an acetonitrile/heptane mixture is used as extractant.

* * * * *